United States Patent [19]

Gordon

[11] Patent Number: 4,461,833

[45] Date of Patent: Jul. 24, 1984

[54] CHROMATOGRAPHICALLY PURIFYING PROTEOLYTIC PROCOAGULANT ENZYME FROM ANIMAL TISSUE EXTRACT

[75] Inventor: Stuart G. Gordon, Denver, Colo.

[73] Assignee: University Patents, Inc., Norwalk, Conn.

[21] Appl. No.: 391,278

[22] Filed: Jun. 23, 1982

[51] Int. Cl.³ .......................... C12Q 1/38; C12Q 1/56
[52] U.S. Cl. ................................... 435/183; 210/656; 435/212; 435/217; 435/219; 435/226; 435/815; 436/543; 436/547; 436/813
[58] Field of Search ............... 435/183, 212, 217, 219, 435/226, 815; 210/656

[56] References Cited

U.S. PATENT DOCUMENTS

| | | | |
|---|---|---|---|
| 3,515,641 | 6/1970 | Whitaker | 435/212 X |
| 4,252,902 | 2/1981 | Fujii | 435/226 X |
| 4,264,738 | 4/1981 | Stepanov | 435/226 X |
| 4,374,926 | 2/1983 | Stern | 435/219 X |
| 4,393,140 | 7/1983 | Schutt | 435/226 |

*Primary Examiner*—Sidney Marantz
*Attorney, Agent, or Firm*—George M. Yahwak; Barbara A. Shimei

[57] ABSTRACT

A chromatographic procedure for the purification of a proteolytic procoagulant enzyme from extracts of human and animal tumors. The extracts are sequentially contacted with a first benzamide affinity chromatographic resin, an agarose filtration gel, a second benzamide affinity chromatographic resin and a phenyl-sepharose hydrophobic chromatographic resin. The resulting enzyme is capable of producing anti-procoagulant antibody which, which used in an immunoassay, is diagnostic for malignancy.

4 Claims, No Drawings

CHROMATOGRAPHICALLY PURIFYING PROTEOLYTIC PROCOAGULANT ENZYME FROM ANIMAL TISSUE EXTRACT

The association between abnormal fibrin metabolism and malignant diseases has been recognized for some time. Fibrin, for example, is known to be deposited at the advancing margin of solid tumors, and on blood-borne malignant cells which are thought to be metastatic. Many researchers have, in fact, reported the administration of anti-coagulants and fibrinolysins to decrease both tumor growth and metastases. These findings have led several investigators to look for procoagulant substance from malignant tissues which might play a role in fibrin deposition and vascular thrombosis observed in cancer patients. If this procoagulant substance could be identified and inhibited, it is believed that this might lead to a treatment for the disease.

The original efforts of O'Meara and his associates, reported in the *Irish Journal of Medical Science* (Volume 394; page 474; 1958), led to the isolation of a thermolabile thromboplastic lipoprotein substance which subsequent studies, reported in the *European Journal of Cancer* (Volume 3; page 467; 1968), showed to be composed of long chain free fatty acids associated with serum proteins such as albumin.

In more recent work (*Journal of Laboratory Clinical Medicine;* 82:255; 1963), Pineo and his collaborators were able to partially purify a glycoprotein from the mucus of nonpurulent chronic bronchitis secretions, ovarian cyst fluid, and saliva that appears to activate blood Factor X; although they did not study malignant tissue sources, they suggested that procoagulant might be responsible for the coagulation phenomenon seen in mucus-secreting adenocarcinomas.

The activation of Factor X by procoagulant can be more easily understood by referring to the following schematic showing the activation of both the intrinsic and extrinsic pathways:

X to Xa. The conversion of Factor X, in turn, by either intrinsic or extrinsic pathways, activates prothrombin (II) to thrombin (IIa) in the presence of calcium, phospholipid, and Factor V. Thrombin converts fibrinogen to fibrin and activates Factor XIII which facilitates fibrin monomer polymerization.

As reported in *Thombosis Research* (Volume 6; page 127; 1975), my initial studies indicated that crude extract isolated from animal carcinomas was not acting on the intrinsic pathway. This could be shown by comparing the clotting times of normal and Factor VIII deficient plasmas. These studies did, however, demonstrate that there was a substance that could be extracted from animal carcinoma that would initiate coagulation by a seemingly unique mechanism, and several studies were run in an effort to define the site of action of this procoagulant.

Since the normal mechanism for tissue associated activation of the coagulation system is the release of tissue factor from damaged cells, it was important to establish that cancer procoagulant was not tissue factor or associated with the extrinsic pathway. My initial studies showed cancer procoagulant initiated coagulation in the absence of Factor VII, and that it was inhibited by the serine protease inhibitor diisopropylfluorophosphate, two characteristics that clearly distinguish it from tissue factor.

Although the general characteristics of cancer procoagulant were able to be demonstrated using tissue extracts from malignant tissues or tissue cultures, without a purification method that was capable of yielding relatively pure proteolytic procoagulant enzyme, it was not possible to identify or test the components of the extract to determine the physical, chemical, and enzymatic properties of the procoagulant, or to attempt to make a coagulant specific antibody for use in the development of an enzyme immunoassay for the detection of the procoagulant in persons suspected of having cancer.

It is an object of the present invention, therefore, to develop a purification procedure for proteolytic procoagulant enzyme.

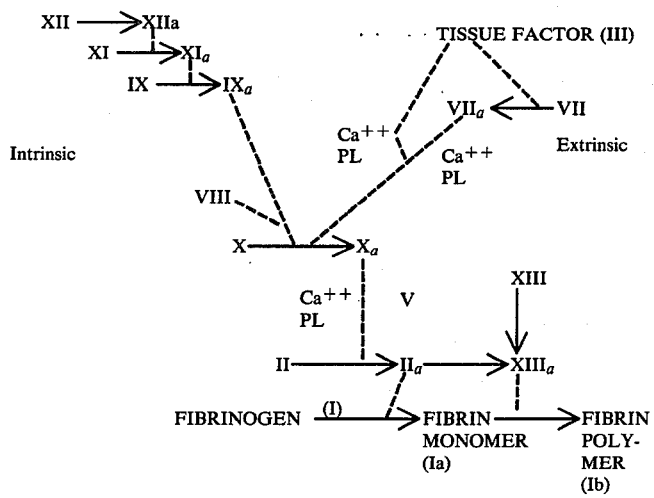

Activation of the intrinsic pathway by surface contact causes Factor XII to form Factor XIIa, which, acting through the proteolytic conversions of Factors XI and Ix, results in an active complex composed of Factor IXa, Factor VIII, calcium and phospholipid, all of which facilitates the proteolytic activation of Factor It is another object of the present invention to demonstrate that the purified proteolytic procoagulant enzyme is capable of stimulating antibodies to the enzyme in host animals.

It is another object of the present invention to demonstrate that the antibody to the purified proteolytic procoagulant enzyme may be collected, purified, and used as a diagnostic test reagent for the determination of the enzyme in body fluids.

The purification of the proteolytic procoagulant according to the present invention is a four step chromatographic technique involving a benzamadine-Sepharose column (step 1); a 1.5M Agarose column (step 2); a benzamadine-Sepharose column (step 3); and a phenyl-Sepharose column (step 5). In addition, a more preferred separation technique is by the use of an additional p-chloromercurial benzoate-Sepharose column as step 4; it is this preferred separation technique which will be discussed below.

The following examples are presented in order for a more thorough understanding of the subject matter and experimental procedure of the present application, are meant to illustrate the embodiment of the present invention, and are not to be construed as limiting the scope of the invention.

EXAMPLE 1

Materials:

A 0.5M stock solution of diisopropylfluorophosphate (DFP) was prepared in dry isopropyl alcohol and diluted 1:100 in samples for DFP treatment. Crude phospholipid was obtained by chloroform-methanol (3:1) extraction (see *Canadian Journal of Biochemical Physiology*; 37:911; 1959) of Rabbit V2 carcinoma. Rabbit brain thromboplastin and Russell's viper venom were used as standards in the coagulation system and as representative procoagulants for comparison of the enzymatic properties with cancer procoagulant. Crude rabbit brain cephalin, veronal buffer and bovine plasma deficient in factors VII and X were commercially purchased. Four parts of fresh bovine plasma were collected in one part 3.8% sodium citrate after discarding the first blood through the needle and centrifuged twice for 5 minutes at 1600 xg to remove blood cells.

EXAMPLE 2

Preparation of Separation Columns:

Benzamidine-Sepharose affinity resin was prepared by coupling ε-amino caproic acid to cyanogen bromide activated Sepharose and 100 mg of p-aminobenzamidine was coupled to 2 gm of hexanoylsepharose with soluble carbodiimide for 24 hours while maintaining the pH at 4.75. After thorough washing of the resin with distilled water, at $1 \times 11$ cm column was packed and equilibrated with a 10 mM veronal buffer (pH 7.8) containing 50 mM NaCl and 1 mM EDTA. The flow rate of this column was 0.5 ml/min.

A gel filtration column ($1.5 \times 100$ cm) was packed with 1.5M agarose and equilibrated with 10 mM veronal buffer at pH 7.8 containing 0.5 mg/ml of crude phospholipid and then washed free of excess phospholipid with 10 mM veronal buffer (pH 7.8). The flow rate of this column was about 1 ml/min.

A phenyl-Sepharose hydrophobic chromatography column ($1 \times 5$ cm) was equilibrated in 10 mM veronal buffer (pH 7.8) containing 0.5 mg/ml of crude phospholipid, washed free of excess phospholipid with the veronal buffer and finally equilibrated with 10 mM veronal buffer (pH 7.8). The column was used at a flow rate of 0.2 ml/min.

A p-chloromercurialbenzoate-agarose affinity resin was prepared by equilibration of the resin in 25 mM 2[N-morpholine]-ethane sulfonic acid buffer at pH 6.8. The equilibrated resin was packed in a $1 \times 10$ cm column and run at a flow rate of about 1.0 ml/minute.

All column chromatography elutions were monitored at 280 nm, and the protein content of aliquots of pooled fraction samples from each step of the purification was routinely determined.

EXAMPLE 3

Source of Cancer Procoagulant:

V2 carcinoma cells were injected into the thigh muscle of young (2 kg) New Zealand white rabbits and the animal's weight and tumor size were monitored bi-weekly until the animal's weight began to decline and the tumor was large. The tumor was removed surgically prior to the animal's death. Tumors ranged in size from 50 to 200 gms. Tumor tissue was cut into 0.5 to 1 cm thick slices to increase surface area and extracted by placing it in 3 changes of 20 mM veronal buffer (pH 7.8) for 3 hours each. The factor VII depleted bovine plasma was used to determine the dependence of the procoagulant activity on Factor VII, using Russell's viper venom and rabbit brain thromboplastin as positive and negative controls, respectively. DFP sensitivity and activity in Factor VII-depleted bovine plasma were two criteria used throughout the purification procedure as identifying characteristics of the enzyme and to distinguish cancer procoagulant from normal tissue thromboplastin.

A two-stage coagulation assay was used to determine the direction activation of pure bovine Factor X by cancer procoagulant. The first stage contained 0.64 μg of purified bovine Factor X in 0.5 ml of 50 mM Tris-HCL buffer (pH 7.8) containing 10 mM $CaCL_2$ and 0.15M NaCl, 10 μg crude rabbit brain cephalin in 20 μl saline and from 5 to 10 ng of purified cancer procoagulant such that the ratio of cancer procoagulant to Factor X was from 1:60 to 1:128. A portion of the purified samples was adjusted to 5 mM DFP, incubated at 25° C. for 30 minutes and added to the first stage of the assay. Partially purified Russell's viper venon standard was diluted 1:100,000 with saline and used in a ratio of 1:320,000 with Factor X. Aliquots (100 ml) of the first stage reaction mixture were taken at various time intervals, including 0 time, and assayed for Factor Xa activity in the second stage by mixing with 100 μl of bovine plasma depleted of Factor VII and Factor X and 100 μl of 20 mM $CaCl_2$. If any Factor Xa was detected in the Factor X samples, they were treated with 25 mM DFP to inactivate the Factor Xa and then dialyzed to remove the residual DFP prior to its use.

To visually demonstrate the direct proteolytic activation of Factor X by cancer procoagulant, 19 μg of purified bovine Factor X in 15 μl of 50 mM Tris-HCl buffer (pH 7.8) containing 10 mM $CaCl_2$ and 0.15M NaCl, 2.5 μg of crude rabbit brain cephalin in 5 μl of saline was incubated with 0.38 μg of cancer procoagulant. In the control experiment, 13.6 μg of Factor X was incubated with 90 pg of Russell's viper venom in the same reaction conditions. Aliquots (10 μl) were removed at 30 seconds, 5 hours., and 15 hours, 2 μl of 0.05M EDTA were added, and the aliquot was added to ¼ volume of sample buffer without B-mercaptoethanol for analysis on a 12.5% sodium dodecylsulfate-polyacrylamide gel electrophoresis.

EXAMPLE 4

Separation Procedure:

Step 1: The concentrated crude tumor extract was applied to the benzamidine affinity chromatography column and unbound protein was washed from the column with 10 mM veronal buffer (pH 7.9) containing 50 mM NaCl and 1 mM EDTA. The bound protein was eluted with 1.0M propionic acid. The acid elute fractions were brought to pH 7.5 immediately with 4N NaOH or they were collected in an equal volume of 0.5M veronal buffer (pH 8.0) to partially neutralize the propionic acid and then adjusted to pH 7.5 with NaOH. All the DFP sensitive, Factor VII independent procoagulant activity was recovered in the acid eluate. The fractions containing procoagulant were pooled, concentrated about 20 fold on an ultrafiltration (PM-10) membrane and dialyzed against 10 mM veronal buffer (pH 7.8) to remove sodium propionate. The quantitative recovery of the procoagulant activity was greater than 100%, probably due to the removal of protease inhibitors present in the tumor extract.

Step 2: The concentrated, dialyzed acid elution peak from the affinity column with a protein concentration of from 6 to 10 mg/ml, was applied to a 1.5M agarose gel filtration column. The column was eluted with 10 mM veronal buffer (pH 7.8); the elution profile had four major protein peaks with the high molecular weight peak containing most of the DFP sensitive procoagulant activity. Fractions from the major procoagulant peak were pooled and concentrated about 5 fold by ultrafiltration and carried to the next step in the purification sequence. The recovery of activity from this step was frequently greater than 100% probably due to removal of additional inhibitors.

Step 3: The concentrated procoagulant peak was applied to the benzamidine affinity resin, a small amount of unbound protein was washed from the column with 10 mM veronal buffer (pH 7.8) containing 50 mM NaCl and 1 mM EDTA, and protein adsorbed to either the resin or to bound proteins was removed by washing the column with 0.1% Triton X-100 in 10 mM veronal buffer (pH 7.8). The Triton X-100 was cleared from the column with the initial veronal buffer, 30 mls of 0.05M propionic acid was used to elute weakly bound proteases, including some procoagulant activity, and then 40 mls of 0.5M propionic acid was used to remove the remaining bound proteins. The acid eluates were either adjusted to pH 7.5 immediately, or collected in 0.5M veronal buffer to partially neutralize the propionic acid as described in Step 1. The samples were dialyzed against 10 mM veronal buffer to remove the sodium propionate, and concentrated by ultrafiltration. No procoagulant activity was recovered in the unbound protein sample and little or no activity was recovered with the protein eluted by Triton X-100. About 30% of the procoagulant activity was recovered in the 0.05M acid eluate; the remaining 70% was in the 0.5M acid eluate which was carried to the next step of the purification. Although the acid eluate from this purification step formed a single immunoprecipitin band on immunoelectrophoresis against an antibody to partially purified cancer procoagulant is contained 3 to 4 protein impurities when analyzed by sodium dodecylsulfate-polyacrylamide gel electrophoresis.

Step 4: About 1.0 ml of the sample eluted from the second benzamidine affinity column was applied to the PCMB affinity resin in 20 mM veronal buffer (pH 7.7) and washed onto the column with 40 ml of MES buffer (ph 6.8), 40 ml of 1M urea and 1% Tween 20 in MES buffer, 20 ml MES buffer to clear the urea and Tween from the column, 35 ml of 0.1 mM dithiothreitol, 35 ml of 5 mM dithiothreitol, 35 ml of 10 mM dithiothreitol, and finally 35 ml of 100 mM dithiothreitol to strip the column of residual protein. Protein eluted from the column was continuously monitored at 280 nm. The protein peaks were collected separately and concentrated about 10 fold on an ultrafiltration membrane and dialyzed against MES buffer to remove the dithiothreitol. Protein was eluted in each of the washes; a small amount of procoagulant activity was eluted in 0.1 mM with the major peak of activity in the 5 mM eluate.

Step 5: The concentrated, dialyzed procoagulant sample from the PCMB-Sepharose column was applied to a phenyl-Sepharose hydrophobic affinity column in 10 mM veronal buffer (pH 7.8) containing 10 μg/ml of crude phospholipid. The sample was allowed to equilibrate with the column for 10 minutes and then unbound protein was eluted with 10 mM veronal buffer (pH 7.8). Procoagulant was eluted with 10% dimethyl sulfoxide in veronal buffer, concentrated by ultrafiltration and dialyzed free of dimethyl sulfoxide against veronal buffer. Although about 20% procoagulant activity was recovered in the veronal buffer, dimethyl sulfoxide eluate generally contained most of the remaining 80% of the activity and was a single protein band by sodium dodecylsulfate-polyacrylamide gel electrophoresis.

The separation procedure uses a number of modifications not previously found, or expected, in the conventional separation of proteins:

The second step of the purification procedure utilized the observation that the procoagulant enzyme aggregated when concentrated to more than 2 mg of protein per ml of sample. This permits it to be resolved from other proteins with molecular weights less than 150,000, a molecular weight cut off that is common for most serine proteases. Following gel filtration column chromatography, the benzamidine-affinity chromatography step was repeated, but adsorbed impurities were removed with a nonionic detergent (0.1% Triton X-100) and a low level of propionic acid (0.05M) was used to elute weakly bound proteases, including some cancer procoagulant, before the remaining proteases were stripped from the column with 0.5M propionic acid. A final hydrophobic affinity chromatography step resulted in highly purified protein. The overall purification and recovery were impossible to calculate accurately because inhibitors present in the crude extract masked the procoagulant activity and the instability of the procoagulant resulted in slow but continuous loss of activity. However, the final product of the purification sequence appears to be homogeneous cancer procoagulant enzyme. Also, phospholipid was used to preequilibrate the columns, and routinely added to samples during the purification, including the purified enzyme, because it was demonstrated to improve both the stability and activity of the procoagulant.

EXAMPLE 5

Gel Electrophoresis and Electrofocusing:
Analytical polyacrylamide slab gel electrophoresis was carried out with 10% or 12.5% gels at pH 8.9. Aliquots of samples (4 parts) were added to 1 part of a sample buffer solution containing 10% β-mercaptoethanol, 10% sodium dodecylsulfate, 40% glycerol and 0.01% pyronin Y in 0.125M Tris-base. Non-reduced samples were prepared in the same sample buffer with β-mercaptoethanol omitted. The samples were heated for 2 minutes in boiling water and applied to the gel.

The molecular weight of the pure procoagulant was estimated by determining the electrophoretic migration of proteins with known molecular weight.

Analytical polyacrylamide gel isoelectric focusing was carried out with precast 4% LKB gels according to the standard LKB procedure. The isoelectric point of the pure procoagulant was determined both by the location of proteins of known isoelectric point, and by determining the pH gradient by measuring the pH of 0.1M KCl solution containing 0.5 cm gel slices.

Purified cancer procoagulant appeared as a pair of protein bands on a wide pH range (pH 3.5 to 9.5) analytical polyacrylamide isoelectric focusing gel at a pI of about 4.8 and 4.9. Analysis on a narrow pH range (pH 4.0 to 6.5) gel resolved the pI 4.9 protein band into 2 protein bands, suggesting that there were 3 isozymes of cancer procoagulant.

The amount of procoagulant activity in milliequivalents of rabbit brain thromboplastin (meq RBT) and protein (mg) content of the purification sequence for a representative purification is tabulated in the following Table 1. The specific activity (SA, meq RBT/mg protein), the recovery of activity (%) and the increase in specific activity (purification) were calculated from data obtained. It is believed that recoveries greater than 100% are probably due to the removal of procoagulant inhibitors during purification.

TABLE I

The Results of a Cancer Procoagulant Purification Sequence

| Sample | Total Activity (meq RBT) | Protein (mg) | SA (meq RMB/mg) | % Recovery | Purification (X) |
|---|---|---|---|---|---|
| Crude Extract | 400 | 916.0 | 0.44 | — | — |
| Benz-Aff Chrom 1.5 M Agarose | 1250 | 97.3 | 12.85 | 312.5 | 29.4 |
| Chrom. | 855 | 29.33 | 29.15 | 68.4 | 2.3 |
| Benz-Aff Chrom Phenyl-Seph. | 900 | 5.85 | 153.85 | 105.3 | 5.3 |
| Chrom. | 208 | 0.18 | 1155.6 | 23.1 | 7.5 |
| Net Purification | | | | 52% | 2644.4 |

The enzyme obtained by this purification technique has a molecular weight of about 68,000, and is believed to be a single polypeptide chain since the electrophonetic migration was not affected by recuction with β-mercaptoethanol. When tested by analytical sodium dodecylsufate-polyacrylamide gel electrophoresis, a single protein band was observed. Furthermore, this enzyme differs from other coagulation enzymes in that it activates Factor X. By suspending the purified cancer procoagulant in Freund's adjuvant and injecting it into goats, it has been possible to obtain procoagulant specific antibody which results in a single immunoprecipitin band upon electrophoresis. This antibody can be purified by techniques such as immunoaffinity chromatography and used in the determination of cancer procoagulant in body fluids by conventional RIA or enzyme immunoassay diagnostic protocols.

From the foregoing description, one skilled in the art can easily ascertain the essential characteristics of my invention and without departing from the spirit and scope thereof, can make various changes and/or modifications to the invention for adapting it to various usages and conditions. Accordingly, such changes and modificatons are properly intended to be within the full range of equivalents of the following claims.

Having thus described my invention and the manner and process of making and using it in such full, clear, conside, and exact terms as to enable any person skilled in the art to which it pertains, or with which it is most closely connected, to make and use the same, and having set forth the best modes for carrying out my invention;

I claim:

1. A method for the purification of proteolytic procoagulant enzyme from animal tissue extract containing the enzyme which comprises sequentially contacting the extract with a first benzamide affinity chromatographic resin, a 1.5M agarose filtration gel, a second benzamide affinity chromatographic resin, and a phenyl-sepharose hydrophobic chromatographic resin.

2. The method of claim 1 wherein the extract is contacted with a p-chloromercurialbenzoate-agarose affinity resin after being contacted with the second benzamide affinity chromatographic resin and prior to being contacted with phenyl-sepharose hydrophobic chromatographic resin.

3. The method of claim 1 wherein said first benzamide affinity chromatographic resin, said 1.5M agarose filtration gel, said second benzamide affinity chromatographic resin, and said phenyl-sepharose hydrophobic chromatographic resin are in column form.

4. The method of claim 3 wherein the agarose gel and phenyl-sepharose columns have been preequilibrated with phospholipid.

* * * * *

UNITED STATES PATENT AND TRADEMARK OFFICE
CERTIFICATE OF CORRECTION

PATENT NO. : 4,461,833
DATED : July 23, 1984
INVENTOR(S) : Stuart G. Gordon

It is certified that error appears in the above—identified patent and that said Letters Patent is hereby corrected as shown below:

Column 1, line 5, insert:

--Partial funding for the research disclosed in this instrument was received from the United States Government. The government, as a result of such partial funding, may have an interest in the disclosed technology.--

Signed and Sealed this

Twelfth Day of March 1985

[SEAL]

Attest:

DONALD J. QUIGG

Attesting Officer Acting Commissioner of Patents and Trademarks